United States Patent [19]

Haimovich et al.

[11] Patent Number: 5,578,073
[45] Date of Patent: Nov. 26, 1996

[54] THROMBORESISTANT SURFACE TREATMENT FOR BIOMATERIALS

[75] Inventors: Beatrice Haimovich, North Brunswick, N.J.; Amihay Freeman, Ben Shemen Youth Village, Israel; Ralph Greco, Warren, N.J.

[73] Assignees: Ramot of Tel Aviv University, Tel Aviv, Israel; University of Medicine and Dentistry of New Jersey, Newark, N.J.

[21] Appl. No.: 37,335

[22] Filed: Sep. 16, 1994

[51] Int. Cl.⁶ ............... A61F 2/06; A61F 2/16; C08L 5/08
[52] U.S. Cl. ............... 623/1; 523/112; 523/113; 523/114; 523/115; 524/29; 623/2; 623/6
[58] Field of Search ............... 623/1, 2, 16; 524/29; 523/112, 113, 114, 115

[56] References Cited

U.S. PATENT DOCUMENTS

| | | | |
|---|---|---|---|
| 3,962,158 | 6/1976 | Mima et al. | 524/29 |
| 4,311,573 | 1/1982 | Mayhan et al. | |
| 4,321,711 | 3/1982 | Mano | 3/1.4 |
| 4,326,532 | 4/1982 | Hammar | 623/1 |
| 4,787,900 | 11/1988 | Yannas | 623/1 |
| 4,978,481 | 12/1990 | Janssen et al. | |
| 5,028,597 | 7/1991 | Kodama et al. | 623/1 |
| 5,053,048 | 10/1991 | Pinchuk | |
| 5,197,977 | 3/1993 | Hoffman et al. | 623/1 |
| 5,263,992 | 11/1993 | Guire | 623/1 |
| 5,346,935 | 9/1994 | Suzuki et al. | 524/29 |
| 5,420,197 | 5/1995 | Lorenz et al. | 523/122 |

FOREIGN PATENT DOCUMENTS

| | | |
|---|---|---|
| 230635 | 8/1987 | European Pat. Off. |
| 3-109930 | 5/1991 | Japan |
| 5-9393 | 1/1993 | Japan |
| 5-168878 | 7/1993 | Japan |

OTHER PUBLICATIONS

Malett, et al., "Chitosan: A New Hemostatic", Annals of Thoracic Surgery, 35, 55–58 (1983).

van der Lei, et al, "Improved Healing of Microvascular PTFE Prosthesis by INduction of a ClotLopes" Plastic & Recon Surg. 84, 960–969 (1989).

Miyake, et al., "New Small–CAliber Antithrombotic Vascular Prosthesis" Microsurgery 5 144–150 (1984).

Callow, A. D., "Current Status of Vascular Grafts", Surg. Clin. No. Amer. 65, 501 (1982).

"Implantation Biology, the Host Response and Biomedical Devices" R. S. Creco (ed. (1944).

*Primary Examiner*—Veronica P. Hoke
*Attorney, Agent, or Firm*—Weiser & Associates, P.C.

[57] ABSTRACT

A biomaterial with a thromboresistant surface and a method for forming same are provided. The thromboresistant surface is comprised of a distinct coating layer of a chitosan-based membrane and a biologically active material. The biologically active material is capable of converting the chitosan membrane coating from a highly thrombogenic to an essentially non-thrombogenic one. The biologically active material can be a polymeric substance, such as polyvinyl alcohol, forming a polymeric blend with the chitosan, or, can be a biological substance, such as serum albumin, embedded in or attached to the chitosan membrane which has been activated with a treatment of glutardialdehyde. The thromboresistant biomaterial is suitable for use in vascular grafts having an inside diameter of less than 6 millimeters.

17 Claims, 1 Drawing Sheet

THROMBORESISTANT SURFACE TREATMENT FOR BIOMATERIALS

BACKGROUND OF THE INVENTION

1. Field of the Invention

The present invention generally relates to medical devices having a blood contacting surface which has thromboresistant properties, more particularly, the invention relates to the surface treatment of medical devices with a thromboresistant coating on the surface which is intended for contacting blood and other body fluids where said coating is composed of a chitosan-based membrane incorporating thromboresistant components affecting surface properties.

2. Description of Related Art

A well-recognized problem in the medical community is the development of a thrombus or blood clot or obstruction that forms when any number of devices are used either within the body or within systems wherein blood or other body fluids are contacted or circulated. Such devices include, for example, catheters, vascular grafts, cardiac pacemaker leads, replacement heart valves, sutures, angioplasty devices, and various blood diagnostic, treatment, and storage systems and may be composed of a variety of biomaterials, for example, metals, polymers, and rubbers.

Of special interest are the approximately 350,000 small vessel bypass grafts performed annually in the United States. The saphenous vein is the choice for small vessel replacement but involves many possible limitations and complications; for example, adequate saphenous vein may not be available due to disease or previous usage. Prosthetic grafts made of expanded polytetrafluoroethylene (ePTFE) or Dacron have been used quite successfully for large vessel replacement but almost uniformly fail when used in sizes of less than 6 mm internal diameters. Callow, A. D., *Current Status of Vascular Grafts,* Surg. Clin. No. Amer. 65, 501 (1982). There is an urgent need for the development of a small vascular prosthesis (about 3–4 mm inside diameter) that exhibit thromboresistance for use in distal extremity bypasses, coronary artery bypasses, and a variety of other vascular access procedures.

The host response to biomaterials at the cellular and molecular level is complex. For example see, *Implantation Biology, The Host Response and Biomedical Devices,* (Greco, R. S. ed. 1994). The composition of the biomaterial surface appears to play an important role in thrombosis. Thrombosis is initiated by the adsorption of plasma proteins on the biomaterial surface. This adsorption results from, and is dependent upon, the physical and chemical properties of the biomaterial surface. For example, Dacron has been shown to have a greater effect on platelet activation than ePTFE, while ePTFE is known to be a stronger stimulator of fibrous hyperplasia. Deposition of plasma proteins on the biomaterial surface mediates platelet adhesion via platelet surface receptors. Surface morphology and chemical characteristics, for example, smoothness and hydrophilicity, have been shown to enhance low plasma protein adsorptive properties. As a consequence of the decrease in plasma proteins deposited on the surface, less adhesive matrix proteins will be available to mediate platelet binding and activation on the surfaces, thus leading to reduced surface-initiated thrombosis.

A variety of approaches have been attempted to increase the thromboresistance of these surfaces. These approaches include the bonding of heparin, albumin, or polyurethanes to the surface, the seeding of endothelial cells onto the surface, and the pretreatment of platelets with adhesion receptor specific monoclonal antibodies. All of these approaches, however, have had limited success.

The known practice of graft polymerization of monomers onto the substrate to form thromboresistant polymers on the surface of biomaterials has several drawbacks. Graft polymerization can affect the original chemical structure of the coated biomaterial and has the danger of toxic low molecular residues of the toxic monomers, as discussed in U.S. Pat. No. 4,978,481 to Janssen et al. and U.S. Pat. No. 4,311,573 to Mayhan et al. The grafting process can be complicated and expensive, e.g., requiring elaborate chemical treatment of the substrate. For example, U.S. Pat. No. 5,053,048 to Pinchuk teaches the pretreatment of a substrate before grafting a polymer; in U.S. Pat. No. 4,978,481 the substrate is pre-treated with ozone before grafting the monomer; and in U.S. Pat. No. 4,311,573 the substrate is pre-treated with ozonization or high energy ionizing radiation before the graft polymerization.

An alternative approach to graft polymerization which is based on absorption of biopolymers has been described. Malette, et al, *Chitosan: A New Hemostatic,* Annals of Thoracic Surgery, 36, 55 (1983) examined the effect of soaking large diameter Dacron vascular grafts in an acidic chitosan solution, a deacetylated derivative of arthropod chitin, as related to the leakage of these grafts. Examination of these grafts at 24 hours revealed no rebleeding. The data establishes that chitosan has thrombogenic properties which induced clot formation rendering the vascular grafts impermeable to blood. Similar thrombogenic properties of chitosan were reported by van der Lei, et al., *Improved Healing of Microvascular PTFE Prostheses by Induction of a Clot Layer: An Experimental study in Rats,* Plastic and Reconstructive Surgery, 84, 960 (1989). In their study ePTFE grafts soaked in a diluted acidic chitosan solution that were implanted into rats were covered with a clot layer, indicative of a highly thrombogenic surface. Both studies demonstrate the thrombogenic properties of chitosan as exhibited by the molecular adsorption of chitosan on the surface of the grafts employed. Neither study reported that the adsorbed chitosan solution formed a distinct coating layer.

In contrast to chitosan's thrombogenic properties, polyvinylalcohol (PVA) has been reported to exhibit non-thrombogenic properties. Miyake et al., *New Small-Caliber Antithrombotic Vascular Prosthesis: Experimental Study,* Microsurgery, 5, 144 (1984), reported that tubes made of polyvinylalcohol were non-thrombogenic. These tubes, however, were not suitable for anastomosis since they were not durable enough to withstand tearing by suture.

What is needed is a biomaterial with a non-thrombogenic surface suitable for use in vascular grafts having an inside diameter of less than 6 millimeters and an inexpensive, efficient means for providing consistent non-thrombogenic properties to the surface of the biomaterial.

The present invention provides a biomaterial with a thromboresistant coating, and a method for preparing same. The features and advantages of this invention will be clearly understood through a consideration of the following description.

SUMMARY OF THE INVENTION

The present invention pertains to the surface treatment of biomaterials for use in medical devices which provides a non-thrombogenic surface as a result of a surface coating with a chitosan-based membrane. The construction of a non-thrombogenic chitosan-based membrane is affected by contacting the biomaterial surfaces with mixtures comprising acidic chitosan solutions, polymer solutions, and non-ionic detergents. Following a stabilization treatment by air drying or cross-linking, the adsorbed film forms a stable membrane that affects both the morphology and the chemical characteristics of the biomaterial surface.

Coated biomaterials obtained using this process exhibit a smoother surface and strong structural morphology with improved chemical surface characteristics resulting in a significant decrease in platelet binding to the surface. This effect may be further improved by bioactive agents that may be embedded in the complex or bound to activated sites on the chitosan membrane.

DETAILED DESCRIPTION OF THE INVENTION

Figure 2:
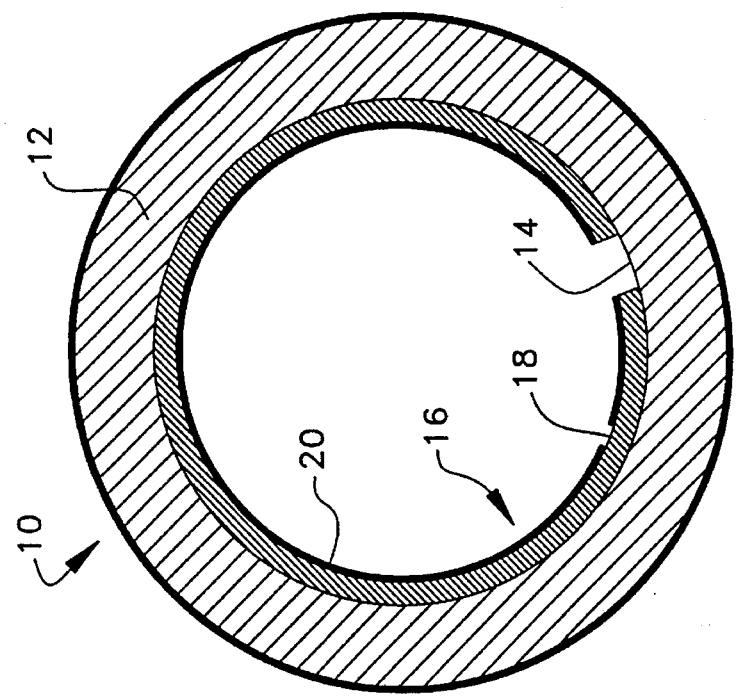
FIG. 2 is a cross-sectional view of an illustration of a vascular graft with another embodiment of the thromboresistant surface of the present invention.

The present invention produces medical devices which are composed of biomaterials having a thromboresistant surface. The thromboresistant properties are provided by a distinct coating layer applied to the surface which comprises a chitosan-based membrane and biologically and/or chemically active materials. The active materials can be incorporated into the chitosan-based membrane and/or bound onto the surface of activated chitosan in the coating layer.

The characteristics of the resulting coating and the method of forming the coating make possible thromboresistant medical devices which could not be manufactured with other coatings and/or methods. For example, vascular grafts with an inside diameter of less than 6 millimeters may now be effectively used and consistently manufactured having a thromboresistant surface according to the present invention.

The process for applying the thromboresistant coating to the biomaterial surface comprises the steps of:

1. Preparing a coating solution comprising a sterile aqueous solution of chitosan with any necessary additives such as hydrophilic polymers, surfactants, stabilizers, buffers, catalysts, and cross-linking agents.
2. The surface of the biomaterial is coated with the coating solution, for example, by pumping or by dipping; any excess solution is removed by draining.
3. The adsorbed solution is cured either by air or gas drying or by chemical cross-linking, using a cross-linking agent in an aqueous solution.
4. If desired, biologically active reagents, such as surfactants, antithrombotic agents, antibiotics or antibodies may be entrapped within the chitosan-based membrane during the initial coating formation or bonded and immobilized to its surface at activated sites on the chitosan after the initial coating formation.

The biomaterials which can be coated include polytetrafluoroethylenes, polyamides, polyesters, polyurethanes, polysioxanes, polyolifins, Dacron, silicone rubber, polyvinyl chlorides, copolymers, metals, and the like. These biomaterials are commonly used in medical devices and prothesis including catheters, vascular grafts, cardiac pacemakers, pacemaker leads, heart diaphragms, heart valves, sutures, needles, angioplasty devices, tubing, dialysis membranes, filters and other artificial implants and machines.

Chitosan is a natural polysaccharide which is soluble in acidic aqueous solutions (pH less than 5.5) and becomes insoluble at physiological pH, with a general structure resembling cellulose. Preferred chitosan concentrations range from about 0.5—3% (w/v). The construction of a chitosan-based membrane on certain biomaterials (for example, ePTFE) may require the incorporation of suitable additives, for example, a non-ionic detergent such as Triton X-100; without which, the chitosan coating solution would be repelled from the ePTFE surface. Due to the presence of free amino groups on the chitosan, it may be readily chemically activated for the chemical binding of bioactive molecules.

Preferred polymer solutions are comprised of about 1–5% (w/v) polyvinyl alcohol (PVA) having a molecular weight between about 10,000 to about 125,000. PVA containing coatings are preferably prepared with aqueous solutions and cured by air drying.

A preferred embodiment of the coating is a complex of chitosan and polyvinyl alcohol (PVA). The PVA is incorporated into the chitosan-based membrane forming a polymer blend. The coating solution for such a chitosan-PVA coating is prepared by adding a PVA solution to the chitosan solution with a chitosan:PVA ratio in the range of about 9:1 to about 1:1. The resulting coating layer unexpectedly exhibits essentially only the desirable qualities of the individual components. The chitosan provides a stable structural base for the incorporation of the PVA. The chitosan-PVA coating exhibits both the strong structural qualities of a chitosan membrane and the thromboresistant qualities of a PVA surface. These chitosan-PVA coatings exhibit none of the thrombogenic properties of chitosan and are significantly more strong and more stable than plain PVA coatings.

A second preferred embodiment of a chitosan-based coating is comprised of a chitosan-based membrane and further comprising one or more bioactive materials, for example antithrombotic agents, antibiotics or antibodies, attached to the chitosan layer at sites which have been activated, for example by glutaraldehyde. The biologically active molecules can also be similarly bound to the thromboresistant chitosan-PVA coatings above.

Figure 1:
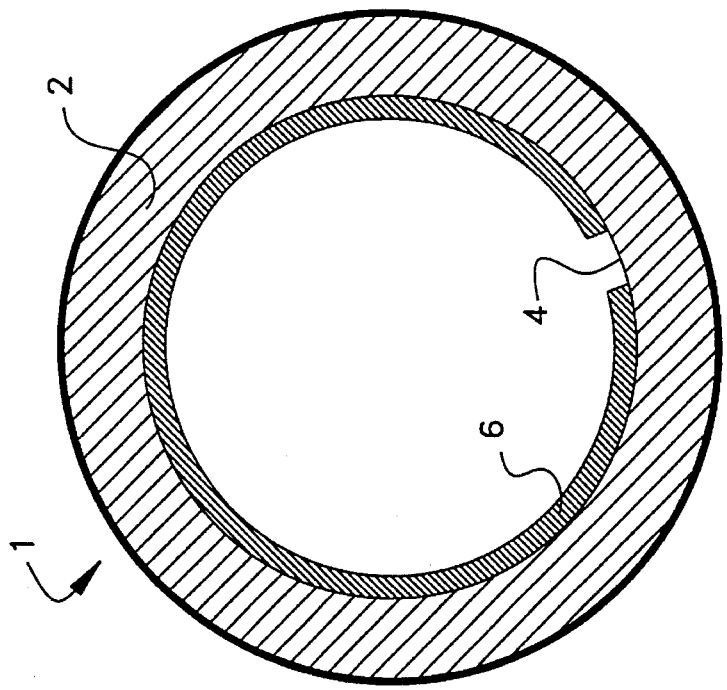
FIG. 1 is a cross-sectional view of an illustration of a vascular graft with a thromboresistant surface of the present invention.

A preferred embodiment of a medical device incorporating the thromboresistant biomaterial is illustrated in FIG. 1 in the form of a vascular graft 1 used for small vessel bypass grafts comprising a section of vascular tubing 2, preferably made of Dacron or ePTFE, having an inside diameter of less than 6 mm, preferably less than 4 mm. On the inner surface of the tubing 4 is a thromboresistant coating 6 comprised of a chitosan-PVA blend.

Another preferred embodiment of a medical device incorporating the thromboresistant biomaterial is illustrated in FIG. 2 in the form of a vascular graft 10 used for small vessel bypass grafts comprising a section of vascular tubing 12, preferably made of Dacron or ePTFE, having an inside diameter of less than 6 mm, preferably less than 4 mm. On the inner surface of the tubing 14 is a thromboresistant coating 16 comprised of a chitosan membrane 18 with a bonded layer of biologically active molecules 20.

The invention is further and more specifically illustrated by the following examples and tests.

EXAMPLE 1

Biomaterials with a thromboresistant coating of PVA were prepared as follows:

Preparation of PVA solution

A 5% (w/v) polymer solution was prepared by stirring 2.5 grams PVA (BDH, Cat. No. 2979) in 50 mLs of warm distilled water. Similar polymer solutions were prepared at concentrations of 0.5%, 1%, and 2.5% (w/v).

Biomaterial Discs

Discs, 6 millimeters in diameter, were prepared by cutting ePTFE cardiovascular straight graft tubes (regular wall tubes, 8 millimeters in diameter Impra, Tempa, AT., USA). Discs were gradually dipped in the 5% (w/v) PVA solution. The discs were removed and excess solution was carefully drained. The coated discs were allowed to dry overnight at room temperature. Additional discs were prepared by independently dipping discs in PVA solutions of differing concentrations of 0.5, 1, and 2.5% (w/v).

EXAMPLE 2

Biomaterials with a thromboresistant coating of a chitosan-PVA coating were prepared as follows.

Preparation of PVA solution

A 5% (w/v) polymer solution was prepared by stirring 2.5 grams PVA (BDH, Cat. No. 2979) in 50 mLs of warm distilled water. Similar polymer solutions were prepared at concentrations of 0.5%, 1%, and 2.5% (w/v).

Preparation of Chitosan Solution

A 3% (w/v) chitosan solution in 1% (v/v) acetic acid was prepared by suspending three grams of chitosan (70,000 MW Fluka CAT. No. 22741) in 99 mLs of water with magnetic stirring for 15 minutes. One mL of glacial acetic acid was then added and mixing continued for 16 hours at room temperature.

Preparation of coating solution

A solution for the preparation of a chitosan-PVA coating containing 1.2% (w/v) chitosan and 0.6% (w/v) PVA was prepared by mixing 4 volumes of 3% chitosan solution with 1.2 volumes of 5% PVA solution. To this solution was added one volume of a 1% (v/v) Triton X-100 (BDH, CAT. No. 30632) and 3.8 volumes of 1% acetic acid.

A second solution for the preparation of a chitosan-PVA coating containing 0.6% (w/v) chitosan and 0.3% (w/v) PVA was prepared by mixing 2 volumes of 3% chitosan solution with 0.6 volumes of 5% PVA solution. To this solution was added 1 volume of a 1% (v/v) Triton X-100 (BDH, CAT. No. 30632) and 6.4 volumes of 1% acetic acid.

Solutions for the preparation of chitosan coatings containing 0.6% (w/v) chitosan and 1.2% (w/v) chitosan were prepared by mixing 4 or 2 volumes of 3% (w/v) chitosan solution with 5 or 7 volumes of 1.0% acetic acid, respecxtively, with 1 volume 1% (v/v) Triton X-100 (BDH, CAT. No. 30632).

Biomaterial Discs

Discs, 6 millimeters in diameter, were prepared by cutting ePTFE cardiovascular straight graft tubes (regular wall tubes, 8 millimeters in diameter Impra, Tempa, AT., USA). Discs were gradually dipped, independently, in either of the chitosano-PVA solutions or chitosan solutions prepared above. The discs were removed and the excess solution was carefully drained. The coated discs were allowed to dry overnight at room temperature.

EXAMPLE 3

Biomaterials with a thromboresistant coating of a Activated Chitosan/Human Serum Albumin coating were prepared as follows.

Preparation of Chitosan Solution

A 3% (w/v) chitosan solution in 1% (v/v) acetic acid was prepared by suspending three grams of chitosan (70,000 MW Fluka CAT. No. 22741) in 99 mLs of water with magnetic stirring for 15 minutes. One mL of glacial acetic acidic was then added and mixing continued for 16 hours at room temperature.

Preparation of chitosan and glutardialdehyde solutions

A diluted chitosan solution (0.6% (w/v)) was prepared by mixing one volume of 3% (w/v) chitosan solution with 4 volumes of 1.0% acetic acid. A 1% (v/v) solution of glutardialdehyde to be used for the activation of a chitosan coating was prepared by mixing one volume of 25% (v/v) glutardialdehyde solution (Merck, CAT. No. 4239) with 24 volumes of standard phosphate buffered saline (PBS) buffer.

Activated Chitosan/Biomaterial Discs

Discs, 6 millimeters in diameter, were prepared by cutting ePTFE cardiovascular straight graft tubes (regular wall tubes, 8 millimeters in diameter Impra, Tempa, AT., USA). Discs were gradually dipped in the 0.6% (w/v) chitosan solution prepared above. A number of the discs were activated (next step) while still wet. The remainder of the discs were dried. A number of the dried discs were set aside and another group were washed with PBS and then set aside.

The chitosan coating, both wet and dry, was then activated by treatment with 1% (v/v) glutardialdehyde in PBS for 15 minutes at room temperature, followed by PBS wash to remove excess of non-bound aldehyde.

The activated coating was then treated with 0.5% (w/v) human serum albumin solution in HANKS medium for one hour at room temperature. Excess non-bound albumin was removed by washing with HANKS medium. Alternatively, as a control, the activated coating was treated with 0.1 M TRIS (Tris[hydroxymethyl]aminomethane) buffer solution to block the aldehyde groups.

EXAMPLE 4

Human blood platelets were isolated and labelled with $^{51}Cr$ as follows:

Platelet binding Assay

Venous blood was collected from healthy human volunteers using protocols approved by the Robert Wood Johnson Medical School Ethics Committee. Human platelets were isolated by gel filtration from freshly drawn blood anti-coagulated with acid-citrate dextrose (56 mM sodium citrate, 65 mM citric acid, 104 mM glucose) supplemented with prostaglandin $E_1$ (1 µM Sigma). Platelet-rich plasma was prepared by centrifugation of the blood at 180×g for 20 minutes at room temperature. Platelets were pelleted from the platelet-rich plasma by centrifugation at 1000×g for 16 minutes at room temperature. The pellet was gently resuspended in platelet-poor plasma. Prostaglandin $E_1$ (1 µM) and apyrase (1 unit/mL Sigma) were added to each isolation step to minimize activation of the platelets. Platelets were isolated from the plasma by filtration through a Sepharose 2B column equilibrated with Walsh buffer (137 mM NaCl, 2.7 mM KCl, 1 mM $MgCl_2$, 3.3 mM $NaH_2PO_4$, 5.6 mM glucose, 20 mM HEPES, 0.1% bovine serum albumin (sigma), pH 7.4). The plasma free platelet count was adjusted to 2–3×10$^8$ platelets/mL using Walsh solution. Platelet quantitation was done using a hemocytometer (Fisher Scientific).

To label platelets with $^{51}$Cr, 500 µCi of $^{51}$Cr (5 mCi/mL normal saline, ICN Biomedicals) was added to each mL of resuspended platelet solution in plasma. The resulting solution was incubated at 37° C. for 60 minutes. The labeled platelets were filtered and diluted as stated above.

TEST 1

Platelet Adhesion Assay

The 6 millimeter coated discs of Example 1 were placed at the bottom of wells in 96-well microtiter plates (Corning). The surface of the discs were coated with platelet-poor plasma (100 µL/well) for one hour at room temperature. Non-adherent proteins were removed by aspiration and the wells were washed three times with phosphate buffered saline (PBS, 200 µL/well). $^{51}$Cr-labelled platelets (100 µL/well) (prepared in Example 4) were added to the wells for one hour. Non-adherent platelets were removed by aspiration and the wells were washed three times with phosphate buffered saline (PBS, 200 µL/well). Adhered platelets were lysed with lysis buffer (2% SDS, 66 mM Tris pH 7.4, 100 µL/well). The lysates were collected and $^{51}$Cr-labelled platelet adherence was quantitated using a gamma counter (LKB Wallac, Model 1282). Each condition was examined in triplicate. Platelet binding to untreated ePTFE discs was normalized in all experiments to 100%. Adhesion to the treated ePTFE surfaces is expressed as percentage binding relative to the binding to the untreated ePTFE surface. Results of different coatings are shown on the following table.

TABLE I

PVA Treatment of ePTFE Discs

| Treatment | % Platelet Binding |
| --- | --- |
| Control - No coating | 100 |
| Coated using a 0.5% PVA solution | 26 |
| Coated using a 1.0% PVA solution | 18 |
| Coated using a 2.5% PVA solution | 20 |
| Coated using a 5% PVA solution | 15 |

Treatment of the ePTFE discs with PVA at concentrations greater than about 1% reduced platelet binding to the surface by 80%.

TEST 2

Platelet Adhesion Assay

The 6 mm coated discs of Example 2 were placed at the bottom of wells in 96-well microtiter plates (Corning). The surface of the discs were coated with platelet-poor plasma (100 µL/well) for one hour at room temperature. Non-adherent proteins were removed by aspiration and the wells were washed three times with phosphate buffered saline (PBS, 200 µL/well). $^{51}$Cr-labelled platelets (100 µL/well) (prepared in Example 4) were added to the wells for one hour. Non-adherent platelets were removed by aspiration and the wells were washed three times with phosphate buffered saline (PBS, 200 µL/well). Adhered platelets were lysed with lysis buffer (2% SDS, 66 mM Tris pH 7.4, 100 µL/well). The lysates were collected and $^{51}$Cr-labelled platelet adherence was quantitated using a gamma counter (LKB Wallac, Model 1282). Each condition was examined in triplicate. Platelet binding to untreated ePTFE discs was normalized in all experiments to 100%. Adhesion to the treated ePTFE surfaces is expressed as percentage binding relative to the binding to the untreated ePTFE surface. Results of different coatings is shown on the following table.

TABLE II

PVA-Chitosan Treatment of ePTFE Discs

| Treatment | % Platelet Binding |
| --- | --- |
| Control - No coating | 100 |
| Coated using a 0.6% chitosan solution | 130 |
| Coated using a 1.2% chitosan solution | 105 |
| Coated using a 0.6% chitosan/0.3% PVA solution | 20 |
| Coated using a 1.2% chitosan/0.6% PVA solution | 15 |

Treatment of the ePTFE surface with the chitosan/PVA mixture reduced platelet binding by 80%. Treatment using only chitosan increased platelet binding to the ePTFE surface.

TEST 3

Platelet Adhesion Assay

The 6 mm coated discs of Example 3 were placed at the bottom of wells in 96-well microtiter plates (Corning). The surface of the discs were coated with platelet-poor plasma (100 µL/well) for one hour at room temperature. Non-adherent proteins were removed by aspiration and the wells were washed three times with phosphate buffered saline (PBS, 200 µL/well). $^{51}$Cr-labelled platelets (100 µL/well) (prepared in Example 4) were added to the wells for one hour. Non-adherent platelets were removed by aspiration and the wells were washed three times with phosphate buffered saline (PBS, 200 µL/well). Adhered platelets were lysed with lysis buffer (2% SDS, 66 mM Tris pH 7.4, 100 µL/well). The lysates were collected and $^{51}$Cr-labelled platelet adherence was quantitated using a gamma counter (LKB Wallac, Model 1282). Each condition was examined in triplicate. Platelet binding to untreated ePTFE discs was normalized in all experiments to 100%. Adhesion to the treated ePTFE surfaces is expressed as percentage binding relative to the binding to the untreated ePTFE surface. Results of different coatings is shown on the following table.

TABLE III

Chitosan Treatment and Post Treatment of ePTFE Discs

| Treatment | % Platelet Binding |
| --- | --- |
| Control - No coating | 100 |
| Coated using a 0.6% chitosan solution/ Drying | 130 |
| Coated using a 0.6% chitosan solution/ Drying, PBS wash | 135 |
| Coated using a 0.6% chitosan solution/ Drying GDA, PBS wash, HSA treatment | 45 |
| Coated using a 0.6% chitosan solution/ | 120 |

TABLE III-continued

Chitosan Treatment and Post Treatment of ePTFE Discs

| Treatment | % Platelet Binding |
|---|---|
| No Drying, GDA, TRIS wash Coated using a 0.6% chitosan solution/ No drying, GDA, PBS wash, HSA treatment | 40 |

GDA — glutardialdehyde
TRIS — Tris[hydroxymethyl]aminomethane buffer
PBS — phosphate buffered saline
HSA — human serum albumin Platelet adhesion to the HSA-chitosan surface was reduced by 50%. Activated TRIS-treated chitosan membrane increased platelet binding to the surface.

While the foregoing description, examples, and tests have disclosed embodiments of the invention in considerable detail for purposes of illustration, it will be understood by those skilled in the art that these details may be varied without departing from the spirit and scope of the invention.

What is claimed is:

1. A biomedical device or prosthesis having a blood contacting surface which has improved antithrombogenic properties and improved strength, which device or prosthesis has a coating which comprises a blend of chitosan and polyvinyl alcohol wherein the biomedical is a homopolymer or a copolymer selected from the group consisting of polytetrafluoroethylenes, polyamides, polyesters, polyurethanes, polysiloxanes, polyolefins, silicone rubber, polyvinyl chlorides, and metals.

2. The biomedical device or prosthesis of claim 1 wherein a portion of the device is tubular.

3. The biomedical device or prosthesis of claim 2 wherein the interior diameter is less than 4 mm.

4. The biomedical device or prosthesis of claim 1 which is selected from the group consisting of catheters, vascular grafts, cardiac pacemakers, pacemaker leads, heart diaphragms, heart valves, sutures, needles, angioplasty devices, tubing, filters, and dialysis membranes.

5. A biomaterial which has improved antithrombogenic properties and improved strength, which biomaterial has a coating which comprises a blend of chitosan and polyvinyl alcohol wherein the biomaterial is a homopolymer or a copolymer selected from the group consisting of polytetrafluoroethylenes, polyamides, polyesters, polyurethanes, polysiloxanes, polyolefins, silicone rubber, polyvinyl chlorides, and metals, which biomaterial is for use in a device or prosthesis having a blood contacting surface.

6. The biomaterial of claim 5 which is a metal.

7. A biomaterial which has improved antithrombogenic properties and which has a coating which comprises chitosan and as a biologically active material which active material is attached to the chitosan at glutaraldehyde-activated free amino sites, human serum albumin.

8. The biomaterial of claim 7 which is a homopolymer or a copolymer selected from the group consisting of polytetrafluoroethylenes, polyamides, polyesters, polyurethanes, polysiloxanes, polyolefins, silicone rubber, polyvinyl chlorides, and metals.

9. A process for treating a biomaterial for use in a biomedical device or prosthesis which has a blood contacting surface, which has improved antithrombogenic properties and improved strength, comprising contacting the surface of the biomaterial with a mixture of a solution of chitosan and polyvinyl alcohol, removing any excess solution, and curing the remaining solution on the surface, thereby obtaining the improved coating, the biomaterial being a homopolymer or a copolymer selected from the group consisting of polytetrafluoroethylenes, polyamides, polyesters, polyurethanes, polysiloxanes, polyolefins, silicone rubber, polyvinyl chlorides, and metals.

10. The process of claim 9 wherein a portion of the biomedical device or prosthesis is tubular with an interior diameter less than 6 mm.

11. A process for treating a biomaterial for use in a biomedical device or prosthesis which has a blood contacting surface and improved antithrombotic properties, comprising contacting the surface of the biomaterial with a chitosan solution, and activating free amino groups on the chitosan by treating the chitosan on the surface of the biomaterial with a solution of glutaraldehyde, wherein the biomaterial is a homopolymer or a copolymer selected from the group consisting of polyamides, polyesters, polyurethanes, polysiloxanes, polyolefins, silicone rubber, polyvinyl chlorides, and metals and treating the activated chitosan with a biologically active material selected from the group consisting of surfactants, antithrombotic agents, antibiotics, and antibodies.

12. The process of claim 11 wherein the biologically active material is human serum albumin.

13. The process of claim 11 wherein a portion of the biomedical device or prosthesis is tubular with an interior diameter less than 6 mm.

14. A polymeric or metal biomedical device or prosthesis having a blood contacting surface which has improved antithrombogenic properties and improved strength, which device or prosthesis has a coating which comprises a blend of chitosan and polyvinyl alcohol, wherein the device or prosthesis has a portion which is tubular of an interior diameter of less than 6 mm.

15. The device or prosthesis of claim 14 wherein the interior diameter of the tubular portion is less than 4 mm.

16. The device or prosthesis of claim 14 which is selected from the group consisting of catheters, vascular grafts, cardiac pacemakers, pacemaker leads, heart diaphragms, heart valves, sutures, needles, angioplasty devices, tubing, filters, and dialysis membranes.

17. The device or prosthesis of claim 14 which is a graft.

* * * * *